United States Patent [19]

Koch

[11] Patent Number: 5,604,126
[45] Date of Patent: Feb. 18, 1997

[54] MURINE HYBRIDOMA 4A11 AND DIAGNOSTIC ANTIBODY PRODUCED THEREBY

[75] Inventor: Alisa E. Koch, River Forest, Ill.

[73] Assignee: Northwestern University, Evanston, Ill.

[21] Appl. No.: 453,582

[22] Filed: May 26, 1995

Related U.S. Application Data

[63] Continuation of Ser. No. 167,328, Dec. 14, 1993, abandoned, which is a continuation of Ser. No. 864,441, Apr. 6, 1992, abandoned.

[51] Int. Cl.$^6$ .............................. C12N 5/12; C07K 16/28
[52] U.S. Cl. ................... 435/332; 530/388.2; 530/388.1; 935/104; 435/344
[58] Field of Search .................... 435/240.27; 530/388.2, 530/388.1; 935/104

[56] References Cited

PUBLICATIONS

Koch et al, Immunolocalization . . . Tissues, Lab Invest. 64(3):313–320, 1991.
Koch et al, Monoclonal Ab . . . Selectively, Arthritis Rheum 34(9):5156, 1991.
Koch et al Monoclonal Ab . . . Selectively, Clin. Res. 39(2)180A, 1991.
Alles, et al., "Immunohistochemical and Immunochemical Characterization of a New Endothelial Cell–Specific Antigen" J. Histochem. and Cytochem. 34:209–214 (1986).
Bevilacqua, et al. I "Identification of an Inducible Endothelial–Leukocyte Adhesion Molecule" Proc. Natl. Acad. Sci. USA 84:9238–42 (1987).
Bevilacqua, et al. II "Interleukin–1 Activation of Vascular Endothelium: Effects on Procoagulant Axrivity and Leukocuye Adhesion" Am. J. Path. 121:393–403 (1985).
Bevilacqua, et al. III "Endothelial Leukocyte Adhesion Molecule 1: An Inducible Receptor for Neutrophils Related to Complement Regulatory Proteins and Lectins" Science 243:1160–65 (1989).
Butcher, et al. "Organ Specificity of Lymphocyte Migration: Mediation by Highly Selective Lymphocyte Interaction With Organ–Specific Determinants on High Endothelial Venules" Eur. J. Immunol. 10:556–561 (1980).
Carlos, et al. "Membrane Proteins Involved in Phagocyte Adherence to Endothelium" Immunol. Rev. 114:5–28 (1990).
Chin, et al. "A Monoclonal Anti–HEBG$_{pp}$ Antibody With Specificity For Lymphocyte Surface Molecules Mediating Adhesion to Peyer's Patch High Endothelium of the Rat" J. Immunol. 136:2556–61 (1986).

Cotran, et al. "Induction and Detection of a Human Endothelial Activation Antigen in Vivo" J. Exp. Med. 164:661–666 (1986).
Duijvestijn, et al. "Lymphoid Tissue– and Inflammation–Specific Endothelial Cell Differentiation Defined by Monoclonal Antibodies" J. Immunol. 138:713–719 (1987).
Gallatin, et al. "A Cell–Surface Molecule Involved in Organ–Specific Homing of Lymphocytes" Nature 304:30–34 (1983).
Goerdt, et al. "Characterization and Expression Kinetics of an Endothelial Cell Activation Antigen Present in vivo Only in Acute Inflammatory Tissues" Expl. Cell Biol. 55:117–126 (1987).
Hagemeier, et al. "A Monoclonal Antibody Reacting With Endothelial Cells of Budding Vessels in Tumors and Inflammatory Tissues, and Non–Reactive With Normal Adult Tissues" Int. J. Cancer 38:481–488 (1986).
Jalkanen, et al. "A Lymphoid Cell Surface Glycoprotein Involved in Endothelial Cell Recognition and Lymphocyte Homing in Man" Eur. J. Immunol. 16:1195–1202 (1986).
Munro, et al. "Tumor Necrosis Factor and Interferon– $\gamma$ Induce Distinct Patterns of Endothelial Activation and Associated Leukocyte Accumulation in Skin of *Papio Anubis*" Amer. J. Path. 135:121–33 (1989).
Pober, et al. I "Two Distinct Monokines, Interleukin 1 and Tumor Necrosis Factor, Each Independently Induce Biosynthesis and Transient Expression of the Same Antigen on the Surface of Cultured Human Vascular Endothelial Cells" J. Immunol. 136:1680–87 (1986).
Pober, et al. II "Expression of Ia–like Antigens by Human Vascular Endothelial Cells is Inducible in vitro: Demonstration by Monoclonal Antibody Binding and Immunoprecipitation" Proc. Natl. Acad. Sci. USA 79:6641–45 (1982).
Schlingemann, et al. "Monoclonal Antibody PAL–E Specific for Endothelium" Lab. Invest. 52:71–76 (1985).
Scully, et al. "AIDS–Related Kaposi's Sarcoma Displays Differential Expression of Endothelial Surface Antigens" Amer. J. Path. 130:244–251 (1988).
Koch et al, Pathobiol., 1990, 58:241, Reactivity . . . Antigens.
Furukawa et al., Mol. Immunol., 27(8):723, 1990.

*Primary Examiner*—Frank C. Eisenschenk
*Attorney, Agent, or Firm*—Tilton, Fallon, Lungmus & Chestnut

[57] ABSTRACT

Hybridoma 4A11 produces a murine IgM monoclonal antibody specifically against endothelial cells in diseased tissues such as rheumatoid and osteoarthritis synovial tissues, and psoriatic skin. The 4A11 antibody has possible clinical utility for detection of human endothelial cells mainly in inflamed and malignant disease states.

2 Claims, 2 Drawing Sheets

MURINE HYBRIDOMA 4A11 AND DIAGNOSTIC ANTIBODY PRODUCED THEREBY

This invention was made with Government support under Grant Number: AR30692 awarded by NIH. The Government has certain rights in the invention.

This application is a continuation of application Ser. No. 08/167,328 filed Dec. 14, 1993, now abandoned, which was a continuation of application Ser. No. 07/864,441, filed Apr. 6, 1992, now abandoned.

BACKGROUND OF THE INVENTION

1. Field of the Invention

The field of this invention is hybridomas and monoclonal antibodies. More specifically, this invention relates to hybridoma produced monoclonal antibodies that can specifically identify endothelial cells in diseased tissue, and which are useful in the diagnosis of rheumatoid and osteoarthritis synovial tissues and psoriatic skin.

2. Description of the Prior Art

The fusion of mouse myeloma cells and spleen cells from immunized mice by Kohler and Milstein in 1975 (Nature 256:495–497, 1975) demonstrated for the first time that it was possible to obtain a continuous cell line making homogeneous (so-called "monoclonal") antibody. Since this seminal work, much effort has been directed to the production of various hybrid cells (called "hybridomas") and to the use of the antibody made by these hybridomas for various scientific investigations.

Endothelial cells, which form a continuous lining of the vascular systems, perform a variety of functions, including control of coagulation, regulation of platelet function and thrombosis and transport of cells and metabolic components to and from circulation. Much evidence supports the role of vascular endothelial cells in the initiation of inflammatory and immunological responses, including adhesion to circulating leukocytes, stimulation of intravascular coagulation, and presentation of antigen to T lymphocytes.

The rheumatoid (RA) synovium contains numerous new and developing blood vessels, perhaps fueled by angiogenic factors released by macrophages within these tissues. The inflamed endothelium may have different phenotypic and functional characteristics from that found in other noninflamed tissues. For instance, there may be a distinct leukocyte-endothelium recognition system that directs the extravasation of leukocytes into inflamed synovium.

While markers such as monoclonal antibodies (mAbs) BW200, PAL-E, and E431 are pan-endothelial, recent evidence has indicated that vascular endothelial displays phenotypic heterogeneity, as determined by monoclonal antibodies detecting subsets of endothelial cells (Alles, J. U., and K. Bosslet. 1986. Immunohistochemical and immunochemical characterization of a new endothelial cell-specific antigen. J. Histochem. Cytochem. 34:209–214; Hagemeier, H.-H., E. Vollmer, S. Goerdt, K. Schulze-Osthoff, and C. Sorg. 1986. Monoclonal antibody reacting with endothelial cells and budding vessels in tumors and inflammatory tissues, and non-reactive with normal adult tissues. Int. J. Cancer 38:481–488; Schlingemann, R. O., G. M. Dingjan, J. J. Emeis, J. Blok, S. O. Warnaar, and D. J. Ruiter. 1985. Monoclonal antibody PAL-E specific for endothelium. Lab. Invest. 52:71–76; Scully, P. A. H. K. Steinman, C. Kennedy, K. Trueblood, D. M. Frisman, and J. R. Voland. 1988. AIDS-related Kaposi's sarcoma displays differential expression of endothelial surface antigens. Am. J. Pathol. 130:244–251). A monoclonal antibody has been described which reacts preferentially with endothelial cells of capillaries, small and medium sized veins, and venules in normal and tumor tissues (Schlingemann, R. O., G. M. Dingjan, J. J. Emeis, J. Blok, S. O. Warnaar, and D. J. Ruiter. 1985. Monoclonal antibody PAL-E specific for endothelial. Lab. Invest. 52:71–76). Monoclonal antibody EN 7/44 reacts with endothelial cells of budding vessels in human tumors, inflammatory tissues, and placentas, as well as with cultured human umbilical vein endothelial cells (HUVECS), but does not react with endothelial cells of normal tissues (Hagemeier, H.-H., E. Vollmer, S. Goerdt, K. Schulze-Osthoff, and C. Sorg. 1986. Monoclonal antibody reacting with endothelial cells and budding vessels in tumors and inflammatory tissues, and non-reactive with normal adult tissues. Int. J. Cancer 38:481–488 ). Monoclonal antibody 1F10 recognizes an endothelial cell surface antigen abundantly expressed in continuous endothelia, but rarely expressed in liver sinusoidal endothelia (Goerdt, S., G. Zwaldo, R. Schlegel, H.-H. Hagemeier, and C. Sorg. 1987. Characterization and expression kinetics of an endothelial cell activation antigen present in vivo only in acute inflammatory tissue. Exp. Cell. Biol. 55:117–126). In contrast monoclonal antibody 4A11, described here, appears to detect an antigen distinct from those antigens recognized by other monoclonal antibodies, since it does not react with cultured human umbilical vein endothelial cells and is selective for endothelial in synovium, lymphoid tissues, and malignant or inflamed tissues.

Recently, antigens have been detected on endothelial cells which have been activated with stimuli such as cytokines (Munro, J. M., J. S. Pober, and R. S. Cotran. 1989. Tumor necrosis factor and interferon gamma induce distinct patterns of endothelial activation and associated leukocyte accumulation in skin of *Papio anubis*. Am. J. Pathol. 135:121–133; Bevilacqua, M. P., J. S. Pober, D. L. Mendrick, R. S. Cotran, and M. A. Gimbrone. 1987. Identification of an inducible endothelial-leukocyte adhesion molecule. Proc. Natl. Acad. Sci. USA 84:9238–9342). Monoclonal antibody 4D10 reacts with lipopolysaccharide (LPS), tumor necrosis factor-alpha (TNF), interleukin-1 (IL-1) and phorbol myristate acetate (PMA) stimulated cultured human umbilical vein endothelial cells in culture and with endothelial cells in tissues in acute inflammatory conditions, such as atopic dermatitis (Goerdt, S., G. Zwaldo, R. Schlegel, H.-H. Hagemeier, and C. Sorg. 1987. Characterization and expression kinetics of an endothelial cell activation antigen present in vivo only in acute inflammatory tissue. Exp. Cell. Biol. 55:117–126). 4D10 antigen is not present in rheumatoid arthritis (RA) synovial tissues. Antigens such as ELAM-1 are expressed selectively on cultured human umbilical vein endothelial cells stimulated with interlukin-1 or tumor necrosis factor-alpha, but not on resting cultured human umbilical vein endothelial cells (Bevilacqua, M. P., J. S. Pober, D. L. Mendrick, R. S. Cotran, and M. A. Gimbrone. 1987. Identification of an inducible endothelial-leukocyte adhesion molecule. Proc. Natl. Acad. Sci. USA 84:9238–9342; Cotran, R. S., M. A. Gimbrone jr., M. P. Bevilacqua, D. L. Mendrick, and J. S. Pober. 1986. Induction and detection of a human endothelial activation antigen in vivo. J. Exp. Med. 164:661–666; Pober, J. S., and M. A. Gimbrone 1982. Expression of Ia-like antigens by human vascular endothelial cells is inducible in vitro: Demonstration by monoclonal antibody binding and immunoprecipitation. Proc. Natl. Acad. Sci 79:6641–6645; Bevilacqua, M. P., J. S. Pober, M. E. Wheeler, R. S. Cotran, and M. A. Gimbrone Jr. 1985. Interleukin-1 activation of vascular endothelium. Effects on procoagulant activity and leucocyte adhesion. Am. J. Pathol. 121:394–403; Bevilacqua, M. P., S. Stentgelin, M. A. Gimbrone Jr., and B. Seed. 1989. Endothelial leukocyte adhesion molecule 1: an inducible receptor for neutrophils related to complement regulatory proteins and lectins. Science 243:160–1165; Pober, J. S., D. L. Bevilacqua, L. A. Mendrick, W. Fiers, and M. A. Gimbrone Jr. 1986. Two distinct monokines, interleukin 1 and tumor necrosis factor, each independently induce biosynthesis and transient expression of the same antigen on the surface of cultured human vascular endothelial cells. J. Immunol. 136:1680–1687). Endothelial leukocyte adhesion molecule-1 (ELAM-1) is expressed on endothelium in delayed hypersensitivity reactions and on endothelium of inflamed but not normal tissues and in part mediates monocyte adherence to endothelial cells (Cotran, R. S., M. A. Gimbrone jr., M. P. Bevilacqua, D. L. Mendrick, and J. S. Pober. 1986. Induction and detection of a human endothelial activation antigen in vivo. J. Exp. Med. 164:661–666; Carlos, T., and J. M. Harlan. 1990. Membrane proteins involved in phagocyte adherence to endothelium. Immunological Reviews 114:1–28). In contrast, monoclonal antibody 4A11 does not detect an antigen upregulated by stimulation of cultured human umbilical vein endothelial cells with the cytokines examined.

Endothelial cells are strategically located at the interface between the circulation and the extravascular tissues and perform many functions, including control of coagulation and regulation of thrombus formation (Duijvestijn, A. M., M. Kerkhove, R. F. Bargatze, and E. C. Butcher, 1987. Lymphoid tissue and inflammation-specific endothelial cell differentiation defined by monoclonal antibodies. J. Immuno. 138:713–179). One particularly important function of endothelium is its role in mediating leukocyte extravasation from blood into sites of inflammation (Duijvestijn, A. M., M. Kerkhove, R. F. Bargatze, and E. C. Butcher, 1987. Lymphoid tissue and inflammation-specific endothelial cell differentiation defined by monoclonal antibodies. J. Immunol. 138:713–179). For instance, high endothelial venules in mucosal lymphoid organs in nonmucosal lymph nodes, and inflamed synovium, express organ-specific ligands recognized by complementary homing receptor molecules on circulating lymphocytes (Duijvestijn, A. M., M. Kerkhove, R. F. Bargatze, and E. C. Butcher, 1987. Lymphoid tissue and inflammation-specific endothelial cell differentiation defined by monoclonal antibodies. J. Immunol. 138:713–179; Butcher, E. C., R. G. Scollay, and I. L. Weissman. 1980. Organ specific lymphocyte migration: Mediation by highly selective lymphocyte interactions with organ-specific determinants on high endothelial venules. Eur. J. Immunol. 10:556–561; Chin, Y. H., R. A. Rasmussen, J. J. Woodruff, and T. G. Easton. 1986. A monoclonal anti-HEBFpp antibody with specificity for lymphocyte surface molecules mediating adhesion to Peyer's patch high endothelium of the rat. J. Immunol. 136:2556–2561; Gallatin, W. M., E. C. Butcher, and I. L. Weissman. 1983. A cell surface molecule involved in organ-specific homing of lymphocytes. Nature 304:30–34; Jalkanen, S. T., R. F. Bargatze, L. R. Herron, E. C. Butcher. 1986 A lymphoid cell surface glycoprotein involved in endothelial cell recognition and lymphocyte homing in man. Eur. J. Immunol. 16:1195–1202; Rasmussen, R. A., Y. H. Chin, J. J. Woodruff, and T. G. Easton. 1985. Lymphocyte recognition of lymph node high endothelium. VII. Cell surface proteins involved in adhesion defined by monoclonal anti-HEBF$_{LN}$(A.11) antibody. J. Immunol. 135:19–24). Unlike the synovial reactivity of HECA-452, which has been reported by various authors either not to be present in synovial tissue from rheumatoid arthritis patients or to react with both high endothelial venules and synovial dendritic cells, the inventor does not find 4A11 reactivity on rheumatoid arthritis synovial dendritic cells (Jalkanen, S. 1989. Leukocyte-endothelial cell interaction and the control of leukocyte migration into inflamed synovium. Springer Semin. Immunopathol. 11:187–198; van Dinther-Janssen, A. C. H. M., S. T. Pals, R. Scheper, F. Breedveld, and C. J. L. M. Meijer. 1990. Dendritic cells and high endothelial venules in rheumatoid synovial membranes).

SUMMARY OF THE INVENTION

A hybridoma clone, designated 4A11, was produced from the fusion of primed mouse splenocytes and mouse myeloma NS-1 cells. Hybridoma 4A11 produces a murine IgM monoclonal antibody which specifically recognizes endothelial cells in diseased tissue to a greater extent than in normal tissues.

Because of the remarkable specificity of 4A11 for human endothelial cells in diseased tissue, the data suggest 4A11 will be an appropriate reagent for diagnosis and therapy of disease states such as rheumatoid (RA) and osteoarthritis (OA) synovial tissue and psoriatic skin. Additionally, this monoclonal antibody could potentially specifically recognize inflammatory and malignant disease states, such as vascular tumors.

DETAILED DESCRIPTION OF THE INVENTION

Figure 1:
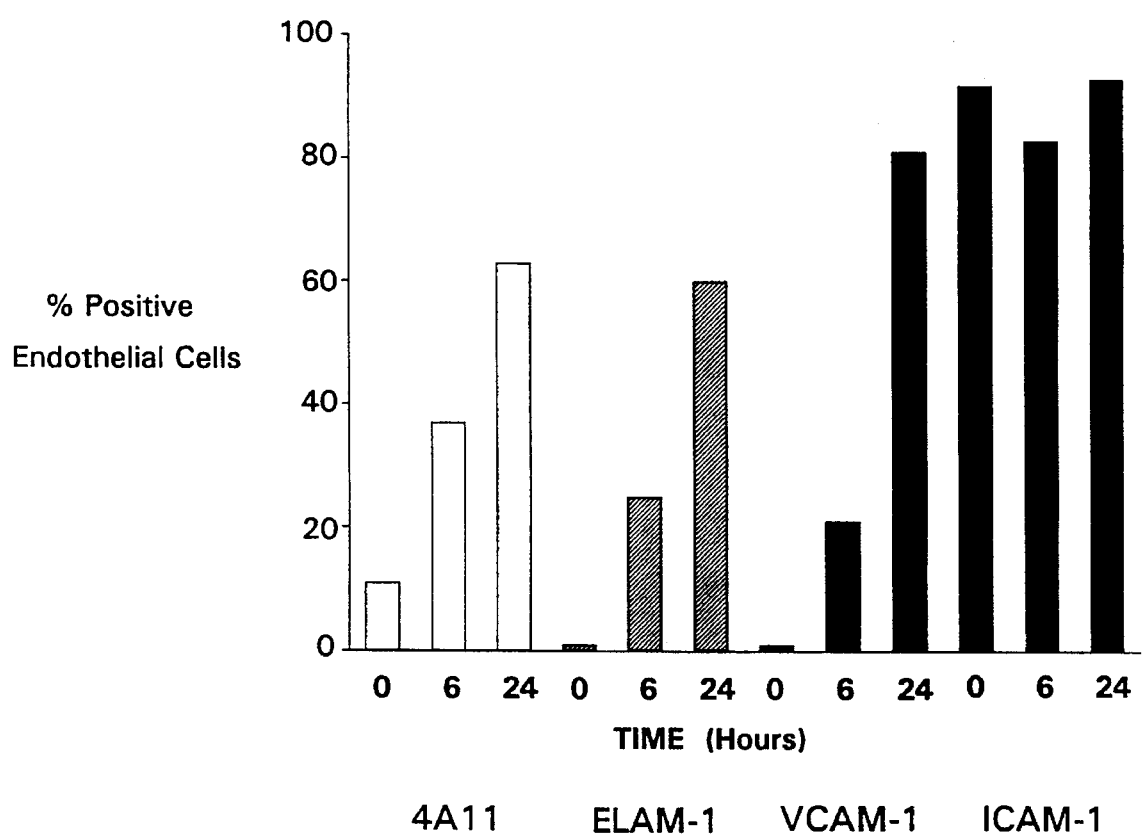
FIG. 1 shows upregulation of 4A11 expression in contact dermatitis.

The antigenic preparation used in obtaining hybridoma 4A11 consisted of a single cell suspension obtained from rheumatoid arthritis synovial tissues that were digested enzymatically. The digested tissue were used to prepare murine hybridoma according to well known procedures. Briefly, hybridoma clone 4A11 was produced by the fusing of mouse myeloma NS-1 cells with BALB/c splenocytes obtained from a mouse hyperimmunized with cells from the digested tissue.

The monoclonal antibody produced by the hybridoma 4A11 was tested to determine the properties and specificity of 4A11. These tests and results are described below.

1. Origin: It was produced by fusion of NS-1 mouse myeloma cells with BALB/c mouse splenocytes primed with a single cell suspension obtained from rheumatoid arthritis synovial tissues that were enzymatically digested.

2. Cultivation: The 4A11 hybridoma can be cultivated in RPMI plus 10% fetal calf serum.

3. Properties: The 4A11 hydridoma is not phytopathogenic and is not known to have any dangerous properties.

4. Antibody: 4A11 produces a murine IgM monoclonal antibody which specifically recognizes endothelial cells mainly in inflamed and malignant disease states. 4A11 monoclonal antibody does not react with the myeloid or lymphoid cell lines studied or with peripheral blood cells. 4A11 monoclonal antibody does not react with platelets. 4A11 monoclonal antibody reacts with most endothelial cells in lymphoid tissue, but with few (less than 11%) endothelial cells in thymus, liver, lung, adrenal, and skin. Monoclonal antibody 4A11 detects endothelial cells in diseased tissues. such as rheumatoid and osteoarthritis synovial tissues, and psoriatic skin. Both vascular adrenal tumors and dermal Kaposi's sarcoma are 4A11 reactive. In vitro, the 4A11 antigen is not present on cultured human umbilical vein endothelial cells, and its expression is not induced in these cells by treatment with lipopolysaccharide, interferon-gamma, interleukin-1,-6 or tumor necrosis factor-alpha. However, in an in vivo model of contact dermatitis, the 4A11 antigen is upregulated differentially from other endothelial markers such as endothelial-leukocyte adhesion molecule-1 (ELAM-1), vascular cell adhesion molecule-1 (VCAM-1), and intercellular adhesion molecule-1 (ICAM-1). In this dermal model of inflammation, poison ivy extract is applied to the skin and biopsies taken at 0, 6 and 24 hours. 4A11 antigen is expressed on 11% of dermal endothelial cells at time 0 and antigen expression increases with time until 24 hours, when 4A11 antigen is present on 63% of the endothelial cells.

5. Testing: The production of 4A11 antibody by hybridoma cells can be tested by indirect immunofluorescence on viable cells, or by immunoperoxidase staining of frozen sections of human lymph nodes.

The 4A11 hybridoma can be propagated in vitro at an initial cell concentration of $2\times10^5$ cells/ml in RPMI medium containing fetal calf serum. The cells are grown in stationary suspension culture at 37° C. in a well-humidified 5% $CO_2$ incubator and are transferred every 3–4 days.

Using the cuturity procedures described above, the 4A11 antibody may also be produced. The antibody is obtained by centrifuging the cell culture medium at 1000 RPM for 7 minutes at 4° C. The supernatant, which contains approximately 10μg/ml of IgM monoclonal antibody, is frozen at −20° C. in small aliquots. Larger yields can be obtained according to the method, described by Hoogenraad et al., "J. Immunol. Methods," 61:317–320 (1983); Goding, "J. Immunol. Methods," 39:285–308 (1980) (hereby incorporated by reference).

EXPERIMENTAL EXAMPLES

The scientific basis of the present invention will be more fully understood from the following description of the research investigations which led to the invention.

MATERIALS AND METHODS

Antigen Preparation

Isolation of human rheumatoid arthritis synovial tissue digest cells

Samples of fresh rheumatoid arthritis human synovial tissues were obtained from patients undergoing total joint replacement. All samples were obtained with Institution Review Board approval. Fresh synovial tissues were minced and digested in a solution of dispase, collagenase and DNase, as previously described (Koch, A. E., Polverini P. J. Leibovich S. J.: Stimulation of neovascularization by human rheumatoid synovial tissue macrophages. Arthritis Rheum. 29:471,1986). The resultant single-cell suspensions were fractionated into density-defined subpopulations of cells enriched in macrophages by isopyknic centrifugation through continuous preformed Percoll gradients (Pharmacia, Piscataway, N.J.). Cells were enriched by adherence to fibronectin-coated collagen gels and selective trypsinization (incubation with trypsin:EDTA for 5–10 minutes). Cells were harvested from the collagen gels by treatment with clostridial collagenase and found to be equal to or greated than 90 percent macrophages.

Immunization Protocol

One eight to twelve week old BALB/c mouse was injected intraperitoneally with $5.3\times10^6$ synovial digest cells enriched in adherent cells by using at 22 gauge needle and plastic syringe. The injection vehicle for the antigen is phosphate buffered saline (pH 7.2–7.4) purchased from the Cancer Center of Northwestern University Medical School. 56 days later, the mouse was reinoculated as above using $3\times10^6$ synovial digest cells. Ninety days later the mouse was injected with $7\times10^6$ synovial digest cells; half of the cells were injected intraperitoneally as before and half were injected intravenously into the mouse tail vein with a 22 gauge needle. Three days after the final injection, the mouse was sacrificed, its spleen removed.

Cell fusion and cloning procedures

Spleen cells were fused with mouse myeloma NS-1 cells at a ratio of 1:2 respectively, by using 40% polyethylene glycol 4000 M.W. Culture supernatants from wells with active growth were tested by immunoperoxidase staining on a battery of frozen and fixed cell lines, isolated peripheral blood cells and normal and inflammatory tissues as described. A monoclonal antibody was intially selected based on its reactivity with endothelial cells in rheumatoid arthritis synovial tissues. By Ochterlony the antibody was determined to be IgM.

Immunoperoxidase staining of cytospin preparations of cell lines and isolated peripheral blood cells Immunoperoxidase staining was used to determine the reactivity of monoclonal antibody 4A11. Four micron sections of frozen tissues were cut, and immunoperoxidase stained using an avidin-biotin technique (Vector Laboratories, Burlingame, Calif.) (Hsu Sm, Raine L. Fanger H: Use of avidin-biotin peroxidase complex (ABC) in immunoperoxidase techniques: A comparision between ABC and unlabeled antibody (PAP) procedures. J. Histochem Cytochem 29: 577, 1981; Koch A. E., Burrows J. C., Haines G. K., Carlos T. M., Harlan J., Leibovich S. J.: Immunolocalization of leukocyte and endothelial adhesion molecules in human rheumatoid and osteoarthritis synovial tissue. Lab Invest 64: 313,1991). Slides, air dried for 2–16 hours, were fixed in cold acetone for twenty minutes. Endogenous peroxidase activity was quenced by incubating the slide for thirty minutes in 0.3% hydrogen peroxide in methanol. All subsequent incubations were performed for fifteen minutes at 37° C. in a moist chamber. The tissue sections were pretreated with 50 μl diluted normal horse serum (135 μl horse serum in 10 ml 1% phosphate buffered saline-bovine serum albumin), incubated with monoclonal antibodies and washed twice. The slides were incubated with a 1:400 dilution of anti-mouse biotinylated antibody in phosphate buffered saline-bovine serum albumin, twice washed with phosphate buffered saline, incubated with avidinbiotinylated horseradish peroxidase complex, and washed twice with phosphate buffered slaine. Slides were then stained with diaminobenzidine tetrhydrochloride substrate for five minutes at room temperature, rinsed in tap water for two minutes, counterstained with Harris' Hematoxylin, and dipped in saturated lithium carbonte solution for bluing.

Monoclonal antibody 4A11 reacted with endothelial cells in frozen tissue sections. The effects of fixation on the 4A11 antigen in paraffin-embedded tissues is shown in Table 1.

TABLE I

Immunoperoxidase reactivity of endothelial cells stained with IgM monoclonal antibody 4A11 in fixed, paraffin-embedded tissues

| Fixative | Monoclonal antibody 4A11 |
|---|---|
| 1. Formalin | |
| A) Rheumatoid arthritis synovial tissue | − |
| 2. Methanol-Carnoy's | |
| A) Rheumatoid arthritis synovial tissue | + |
| 3. OMNIFIX (Xanex Co.) | |
| A) Lymph node | + |
| B) Rheumatoid arthritis synovial tissue | + |

Though no reactivity was detected using formalin fixed, paraffin-embedded tissues, reactivity was present in OMNIFIX and methanol-Carnoy's fixed tissues.

The reactivity of monoclonal antibody 4A11 was compared with the reactivity of a monoclonal antibody detecting factor VIII-related antigen (in antibody FVIII). Monoclonal antibody FVIII was selected as a comparison antibody since it reacts with most endothelial cells in culture as well as most endothelium in a variety of frozen human tissues. Monoclonal antibody 4A11 did not react with myeloid or lymphoid cell lines (Table II).

TABLE II

Monoclonal antibody reactivity to cell lines and cell suspensions as determined by immunohistochemistry

| | Monoclonal Antibody 4A11 | Monoclonal Antibody FVIII |
|---|---|---|
| 1. Cell lines | | |
| A) Myeloid | − | ND |
| U937 (histiocytic lymphoma) | | |
| B) Lymphoid cell lines | | |
| a) Raji (lymphoblast-like) | − | ND |
| b) RPMI 6410 (lymphoma-like) | − | ND |
| 2. Cultured human dermal keratinocytes | + | − |
| 3. Human umbilical vein endothelial cells | − | + |
| 4. Human abdominal aortic endothelial cells | + | + |
| 5. Peripheral blood* | | |
| a) Lymphoytes | − | − |
| b) Monocytes | − | − |
| c) Neutrophils | − | − |
| d) Platelets | − | + |

ND = not done.
*Represents three separate blood donors.

A distinguishing point between monoclonal antibody FVIII and monoclonal antibody 4A11 was the reactivity of monoclonal antibody FVIII with platelets compared to the lack of reactivity of these cells with monoclonal antibody 4A11. Monoclonal antibody FVIII was selected as the reference antibody since it is "the gold standard" for staining endothelial cells in that it reacts with most endothelial cells in most human organs. Additionally, immunohistochemically, monoclonal antibody 4A11 did not react with cultured human umbilical vein endothelial cells, while monoclonal antibody FVIII reacted with these cells. However, while monoclonal antibody 4A11 did not react with immature cultured human umbilical vein endothelial cells, mature cultured human abdominal aortic endothelial cells were 4A11+.

Immunoperoxidase staining of normal frozen tissues

Table III shows the results of staining of normal frozen human tissues with the monoclonal antibody. Monoclonal antibody FVIII reactivity was present in all tissues examined. This was in sharp contrast to monoclonal antibody 4A11, which reacted with endothelium in lymph node and tonsil, but not thymus, spleen, liver, lung, pleural lining, skin, or kidney. Generally, no other cell types, such as macrophages, lymphocytes, or fibroblasts, were reactive with monoclonal antibody 4A11.

TABLE III

Monoclonal antibody reactivity with endothelium of frozen normal human tissue sections as determined by immunohistochemistry

| | Monoclonal Antibody 4A11 | Monoclonal Antibody FVIII |
|---|---|---|
| 1. Lymph node | + | + |
| 2. Tonsil | + | + |
| 3. Thymus | − | ND |
| 4. Spleen | − | + |
| 5. Liver | | |
| a) portal vein | − | + |
| b) portal artery | − | + |
| c) central vein | − | + |
| d) sinusoids | − | − |
| 6. Lung | −* | + |
| 7. Pleural lining | − | + |
| 8. Kidney | | |
| a) endothelial cells of glomeruli | − | + |
| 9. Medium sized muscular artery | | |
| a) intima | − | + |
| b) vaso vasorum | −** | + |
| 10. Adrenal gland | − | + |

Abbreviations used: ND = not done
One to three samples of each tissue were assayed.
*In one of two samples tested, less than 20% of blood vessels were stained.
**In one sample tested, 15% of blood vessels stained.

Monoclonal antibody reactivity in synovial tissues

Since monoclonal antibody 4A11 reacted consistently with endothelial cells in human synovial tissues, twenty samples were analyzed in greater detail. Table IV depicts the reactivity of monoclonal antibody 4A11 on synovial tissue samples from normal patients, as well as from patients with rheumatoid arthritis, osteoarthritis and avascular necrosis of the hip.

TABLE IV

Monoclonal antibody 4A11 reactivity is synovial tissues as determined by tissue immunohistochemistry

|  |  | Percent of tissues expressing 4A11 | Percent of vessels expressing 4A11 (mean ± S.E.) | Mean inflammatory score* | Mean vascular score# |
|---|---|---|---|---|---|
| 1) | RA synovial issue (n = 11) |  | 67 ± 9 | 2.4 | 2.0 |
|  | i) Predominant arteriolar staining | 0/11 |  |  |  |
|  | ii) Predominant venular staining | 2/11 |  |  |  |
|  | iii) Equal arteriolar and venular staining | 9/11 |  |  |  |
| 2) | OA synovial tissue (n = 4) |  | 65 ± 18 | 1.0 | 2.2 |
|  | i) Predominant arteriolar staining | 0/4 |  |  |  |
|  | ii) predominant venular staining | 0/4 |  |  |  |
|  | iii) Equal arteriolar and venular staining | 4/4 |  |  |  |
| 3) | Avascular necrosis synovial tissue (n = 1) |  | 70 | 1.0 | 1.0 |
|  | i) Predominant arteriolar staining | 0/1 |  |  |  |
|  | ii) predominant venular staining | 0/1 |  |  |  |
|  | iii) Equal arteriolar and venular staining | 0/1 |  |  |  |
| 4) | Normal synovial tissue (n = 4) |  | 42 ± 15 | 1.3 | 1.5 |
|  | i) Predominant arteriolar staining | 0/4 |  |  |  |
|  | ii) predominant venular staining | 4/4 |  |  |  |
|  | iii) Equal arteriolar and venular staining | 4/4 |  |  |  | n = number of tissue samples assayed. *1 to 4, with 4 representing the greatest mononuclear cell infiltrate.
1 to 4, with 4 representing the greatest number of blood vessels.

Of the tissues examined, the rheumatoid arthritis tissues displayed the greatest amount of inflammatory cell infiltrate. Endothelial cell staining was present in all of the arthritic synovial tissues examined. Monoclonal antibody 4A11 reacted with a mean of 42±15% (S.E.) of the FVIII positive blood vessels in the normal synovial tissue examined, compared to greater numbers (67±9%) of the rheumatoid arthritis and the 65±18% of the osteoarthritis synovial tissue blood vessels. Tissues were analyzed as to reactivity with arteriolar and venular endothelium. In the case of both rheumatoid arthritis and osteoarthritic tissue, most of the tissue displayed approximately equal arteriolar and venular staining within a given tissue. The staining was present on the luminal surface of the vessels. No correlation was found between the number of blood vessels or the inflammatory score and the presence of monoclonal antibody 4A11 reactivity. No increased monoclonal antibody 4A11 reactivity was detected in the blood vessels running through lymphoid aggregates or high endothelial venules.

Monoclonal antibody reactivity with abnormal skin

To determine whether 4A11 antigen expression was upregulated in abnormal skin compared to normal skin biopsies were stained with labeled monoclonal antibody 4A11. The results of staining of skin biopsies with monoclonal antibody 4A11 are shown in Table V.

TABLE V

Monoclonal antibody 4A11 reactivity with pathological skin biopsies

|  |  | Number of tissues staining | Percent of vessels staining (mean ± S.E.) | Mean inflammatory score* | Mean vascular score# |
|---|---|---|---|---|---|
| 1) | Uninvolved skin from psoriatic patients (n = 1) | 0/1 | 0 | 1 | 2 |
| 2) | Psoriatic skin (n = 6) | 6/6 | 37 ± 10 | 2.3 ± 0.2 | 2.2 ± 0.2 |

TABLE V-continued

Monoclonal antibody 4A11 reactivity with pathological skin biopsies

|   | Number of tissues staining | Benign blood vessels | Blood vessels within tumor |
|---|---|---|---|
| 3) Kaposi's sarcoma (n = 3) | 3/3 | 54 ± 20 | 33 ± 24 |

*0 to 4, with 4 representing the greatest amount of mononuclear cell infiltrate.
0 to 4 representing the greatest vascularity.

While uninvolved skin from psoriatic patients did not express endothelial 4A11 antigen, a mean of 37±10% of blood vessels in psoriatic skin biopsies expressed 4A11 antigen (FIG. 1). In addition to vascular reactivity, in some normal and diseased skin samples, both hair shaft and rarely keratinocytes reacted with monoclonal antibody 4A11. Similarly, in Kaposi's sarcoma skin biopsies, monoclonal antibody 4A11 reacted with both benign blood vessels and with vessels within the tumors. Kaposi's sarcoma was not reactive with either anti-ELAM-1 or VCAM-1. ICAM-1 vascular reactivity was present but not to the same degree at 4A11 reactivity. FVIII antigen expression was variable in the Kaposi's tumors.

Monoclonal antibody reactivity 4A11 with tissues from other disease states

The results of immunostaining with monoclonal antibody 4A11 on tissues from several disease states are shown in Table VI.

TABLE VI

Monoclonal antibody 4A11 reactivity with endothelial cells in tissues from disease states as determined by tissue immunohistochemistry

|   |   | Monoclonal Antibody 4A11 reactivity | FVIII reactivity |
|---|---|---|---|
| 1. | Sarcoid lymph node | + | + |
| 2. | Parotid gland with chronic sialoadenitis | − | + |
| 3. | Inguinal hernia sac | − | + |
| 4. | Crohn's colitis | − | + |
| 5. | Adrenal tumor | + | + |

One to three samples of each pathological tissue was assayed. Monoclonal antibody 4A11, like monoclonal antibody FVIII reacted with endothelial cells of a lymph node from a patient with sarcoidosis. Monoclonal antibody 4A11, however, did not react with endothelial cells in a parotid gland with chronic sialoadenitis, in an inguinal hernia sac, or in an inflammatory Crohn's colon.

EXAMPLE 1

Expression of 4A11 antigen on skin endothelial cells in poison ivy dermatitis: comparison with monoclonal antibody 4A11 detecting cell adhesion molecules To determine the expression of 4A11 antigen in an in vivo model of inflammation, a poison ivy/oak mixture (1:50 w:v) in alcohol (Hollister-Steir, Elkhart, Ind.) was applied to the skin of healthy volunteers using the ALTEST System (Sodertalje, Sweden). The extract was applied on the flexor forearm and the patch-test site biopsied at 0 (preapplication), 6, and 25 hours after application of the allergen. Biopsies were snap frozen. Tissue expression of 4A11 antigen was contrasted with expression of ELAM-1, VCAM-1 and ICAM-1. After staining with monoclonal antibody 4A11, anti-ELAM-1, or anti-VCAM-1, and anti-ICAM-1 monoclonal antibody using immunohistochemistry, tissues were scored as to the percentage of endothelial cells reactive with each monoclonal antibody.

In the poison ivy contact dermatitis model, during the first 24 hours after poison ivy extract application, light skin erythema appears as well as a mininal increase in leukocyte infiltrate composed mainly of perivascular lymphocytes. During the period encompassing 2 to 7 days after application, the skin becomes erythematous with vesicle formation and edema. There is a concomitant increase in cellular infiltrate with prominent perivascular and interstital dermal collections of lymphocytes, monocytes, and macrophages. The results of immunoperoxidase staining of skin biopsies are depicted in FIG. 1. In contrast to the vascular expression of ELAM-1 and VCAM-1 which were absent at 0 hours after application (baseline), there were a small number (11±5) (S.E.) of 4A11 positive blood vessels present. 4A11 antigen expression, like ELAM-1 and VCAM-1 expression, increased steadily over 24 hours, until 63+5% of blood vessels were 4A11 reactive. At 24 hours after application, ELAM-1 expression was comparable with 60% of blood vessels staining. VCAM-1 expression was slightly greater at 24 hours with 81±4% of blood vessesl staining. In contrast, ICAM-1 expression remained high (83–93% of blood vessels staining) throughout the 24 hour period.

In this model, the 4A11 antigen is present on only 11% of blood vessels as the time of application of poison ivy extract, and increases steadily until approximately two thirds of blood vessels express this antigen 24 hours after extract application. These events occur prior to intense dermal mononuclear cell infiltration. In contrast, the cellular adhesion molecule, intercellular adhesion molecule-1 (ICAM-1) is expressed on 83–93% of blood vessels during the first 24 hours of poison ivy extract application. Expression of the cellular adhesion molecules vascular cell adhesion molecule-1 (VCAM-1) and ELAM-1 on endothelial cells increases from no positive cells to 81 and 60% positive cells, respectively, 24 hours after poison ivy extract application. Hence, the time course of antigen expression on endothelium in this model differs between the adhesion molecules examined and 4A11 antigen.

EXAMPLE 2

Monoclonal antibody 4A11 binding to stimulated human umbilical vein endothelial cells To determine whether 4A11 expression could be induced on human umbilical vein endothelial cells by stimulation with cytokines and other immune mediators, human umbilical vein endothelial cells at third passage were incubated in 96 well tissue culture plates until confluence. The cells were then cultured with and without 100 μl of the following additives in endothelial growth medium-umbilican vein containing 2% fetal calf serum for time periods ranging from 4 to 48 hours: lipopolysaccharides (5 μg/ml); and the cytokines interferon-gamma (200 units/ml), interleukin-1 (10 units/ml), tumor necrosis factor alpha (200 units/ml), and interleukin-6 (100 ng/nl). All cultures were performed in an incubator gassed with 5% $CO_2$. After the incubation period, human umbilical vein endothelial cells were used in a cellular radioimmunoassay.

Figure 2:
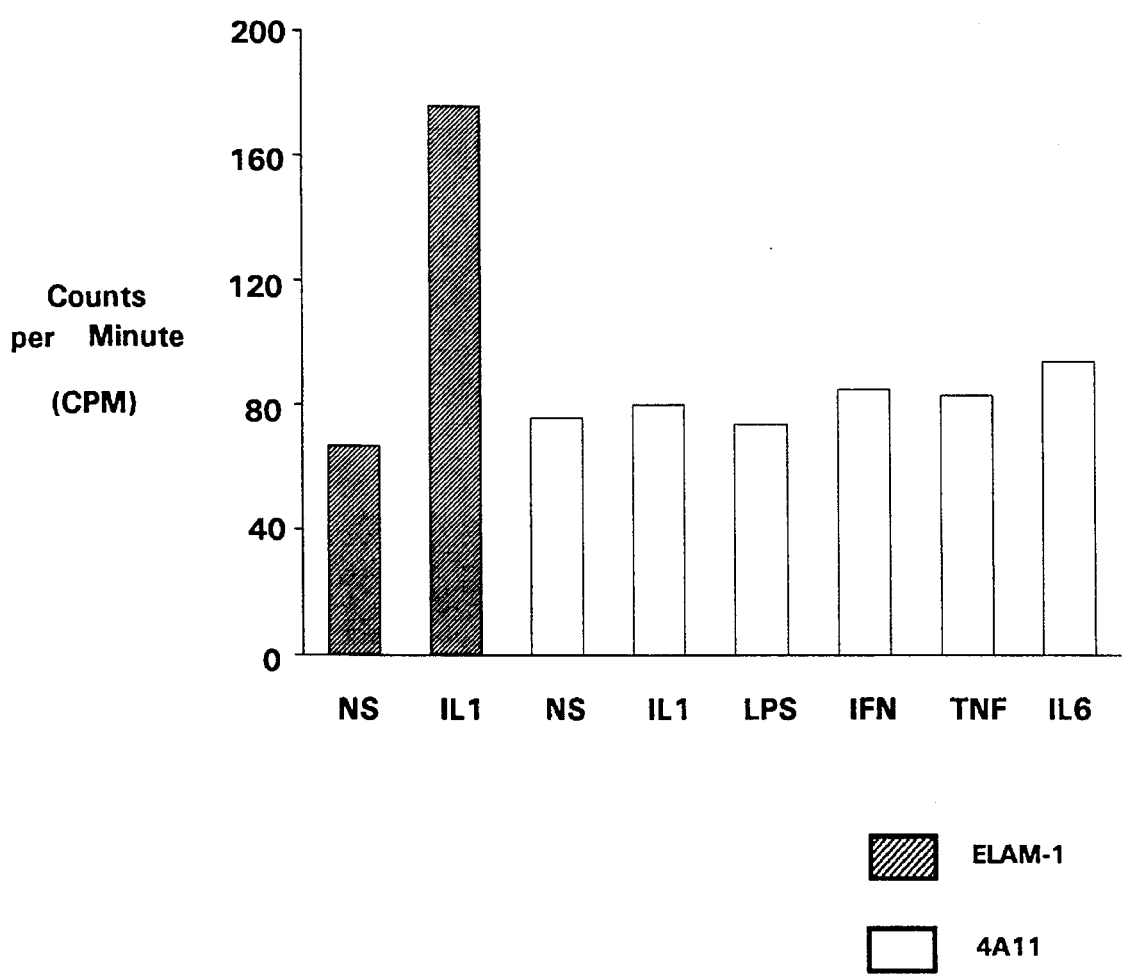
FIG. 2 shows binding of monoclonal antibody 4A11 and ELAM-1 on cultured human umbilical vein endothelial cells (HUVECS) with and without stimulation with lipopolysaccharide (LPS); tumor necrosis factor-alpha (TNF); interleukins-1 and -6 (IL-1, IL-6); interferon-gamma (IFN); and phorbol myristate acetate (PMA). Results shown are a representative experiment with triplicate determinations. Results are represented as the mean±S.E. NS designates nonstimulated, resting cultured human umbilical vein endothelial cells.

The binding of monoclonal antibody 4A11 on human umbilical vein endothelial cells with and without stimulation with lipopolysaccharides and cytokines at four hours is shown in FIG. 2. As can be seen, basal binding of monoclonal antibody 4A11 did not differ significantly from that seen with stimulation of human umbilical vein endothelial cells. In contrast, monoclonal antibody 4A11 ELAM-1 binding peaked at approximately 4–6 hours of stimulation, and deceased thereafter.

EXAMPLE 3

Monoclonal antibody 4A11 reactivity with transfectants bearing ELAM, 1, VCAM-1 or ICAM-1

Chinese hamster ovary cells (CHO) engineered to express single human endothelial antigens were produced. Transfectants expressed either ICAM-1, VCAM-1, or ELAM-1 antigens. Murine ascites containing monoclonal antibody 4A11 was reacted with the chinese hamster ovary cells using an ELISA assay. Monoclonal antibody 4A11, in contrast to control anti-ELAM-1, VCAM-1 or ICAM-1, did not react with chinese hamster ovary cells bearing these antigens. These results indicate that monoclonal antibody 4A11 likely does not recognize any of these known adhesion molecules.

Although the invention has been described primarily in connection with special and preferred embodiments, it will be understood that it is capable of modification without departing from the scope of the invention. The following claims are intended to cover all variations, uses, or adaptations of the invention, following, in general, the principles thereof and including such departures from the present disclosure as come within known or customary practice in the field to which the invention pertains, or as are obvious to persons skilled in the field.

I claim:

1. The hybridoma cell line deposited under ATCC Accession No. HB11274.

2. The monoclonal antibody produced by the hybridoma cell line deposited under ATCC Accession No. HB 11274.

* * * * *